US00PP28766P2

(12) United States Plant Patent
Williams

(10) Patent No.: US PP28,766 P2
(45) Date of Patent: Dec. 12, 2017

(54) ***COLOCASIA* PLANT NAMED 'FIERCE GIGANTE'**

(50) Latin Name: ***Colocasia* hybrid**
Varietal Denomination: Fierce Gigante

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 35 days.

(21) Appl. No.: 14/999,231

(22) Filed: Apr. 12, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Penny J. Aguirre

(57) ABSTRACT

A new cultivar of *Colocasia* plant named, 'Fierce Gigante', that is characterized by its leaves that are large in size, its leaves that are rounded and hastate in shape, its foliage color that is green with a small light violet dot in the center of the leaf, its larger growing habit up to 7 feet in height, its clumping, robust and vigorous plant habit, its petioles that are deep purple in color, its foliage that is held horizontally to upright in aspect, and its root system that is strong and healthy.

2 Drawing Sheets

Botanical classification: *Colocasia* hybrid.
Cultivar designation: 'Fierce Gigante'.

BACKGROUND OF THE INVENTION

The present invention, *Colacasia* 'Fierce Gigante', relates to a new and distinct interspecific hybrid of *Colacasia*, hereinafter referred to by its cultivar name, 'Fierce Gigante'. 'Fierce Gigante' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants that have colorful foliage, a vigorous growth habit, massive plant size and for use in containers and landscapes. 'Fierce Gigante' arose from a cross made in June of 2011 between *Colocasia* 'Cranberry' (not patented) as the female parent and an unnamed and unpatented plant of *Colocasia gigantea* as the male parent. 'Fierce Gigante' was selected as a single unique plant in June of 2014 from amongst the seedlings derived from the above cross.

Asexual propagation of the new cultivar was first accomplished by in vitro propagation using meristem tissue under the direction of the Inventor in Eustis, Fla. in May of 2015. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Fierce Gigante' as a new and unique cultivar of *Colocasia*.

1. 'Fierce Gigante' exhibits leaves that are large in size.
2. 'Fierce Gigante' exhibits leaves that are rounded and hastate in shape.
3. 'Fierce Gigante' exhibits foliage color that is green with a small light violet dot in the center of the leaf.
4. 'Fierce Gigante' exhibits a larger growing habit up to 7 feet in height.
5. 'Fierce Gigante' exhibits a clumping, robust and vigorous plant habit.
6. 'Fierce Gigante' exhibits petioles that are deep purple in color.
7. 'Fierce Gigante' exhibits foliage that is held horizontally to upright in aspect.
8. 'Fierce Gigante' exhibits a root system that is strong and healthy.

'Cranberry', the female parent of 'Fierce Gigante' differs from 'Fierce Gigante' in being shorter in height, in having leaves that are heart shaped with a rippled texture and held downward vertically, in having petioles that are dark maroon in color and in having spreading stolons. *Colocasia gigantea*, the male parent differs from 'Fierce Gigante' in having petioles that are green in color, in having veins on the lower side of the leaves that are green in color, in having flowers that are smaller in size and in having green color at the base of the flowers. 'Fierce Gigante' can be most closely compared to the *Colocasia esculenta* cultivars 'Black Magic' (not patented) and 'Mammoth' (not patented). Both are similar to 'Fierce Gigante' in having large leaves. 'Black Magic' differs from 'Fierce Gigante' in being shorter in height, in having petioles that are dark black to maroon in color, in having leaves that are held downwards from the petiole and in having inflorescences that are smaller in size. 'Mammoth' differs from 'Fierce Gigante' in having leaves that are smaller in size, in having leaves and petioles that are green in color, in having leaves that are held downwards from the petiole and in having spathe flowers that are yellow in color.

BRIEF DESCRIPTION OF THE DRAWINGS

The accompanying colored photographs illustrate the overall appearance and distinct characteristics of 'Fierce Gigante'. The photographs were taken of a plant 3-years in age as grown outdoors in a trial garden in Louisville, Ky.

Figure 1:
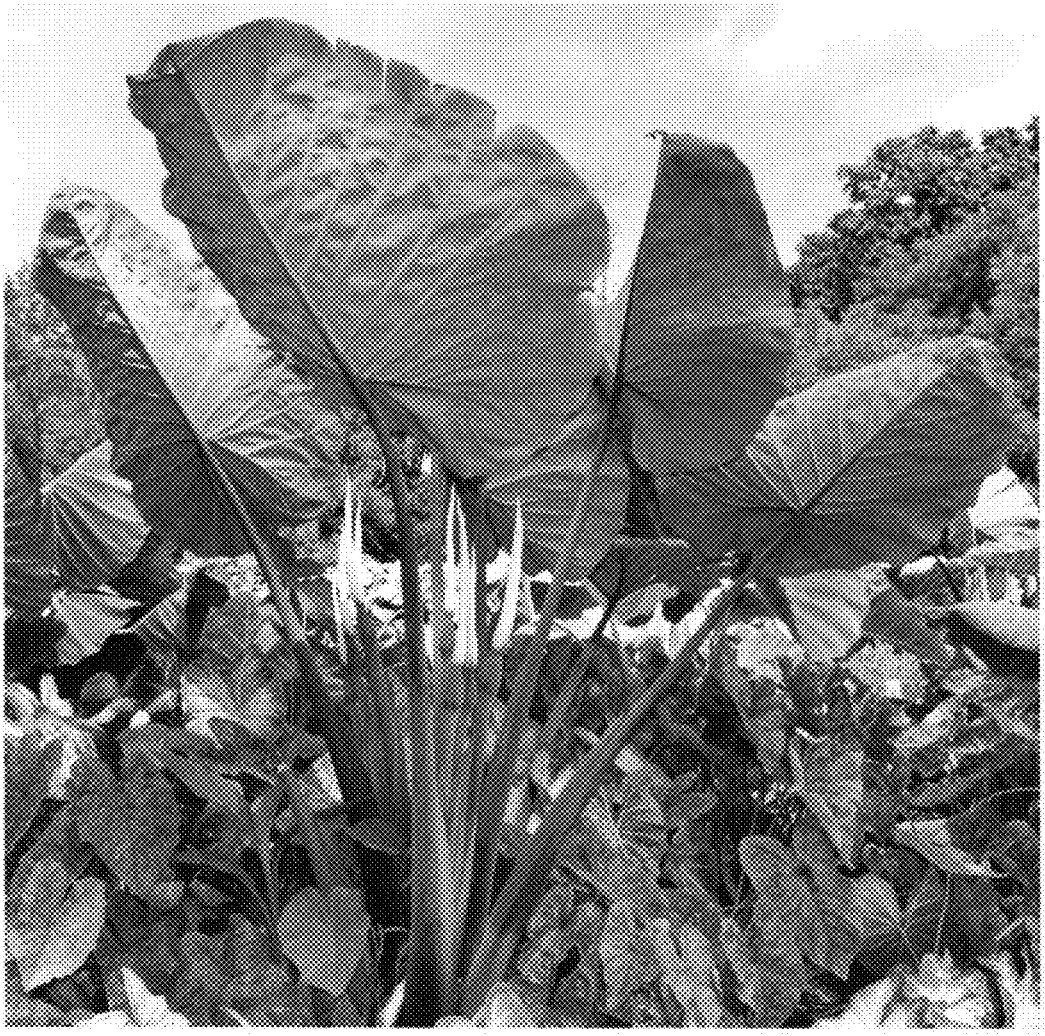
FIG. 1 provides a side view of 'Fierce Gigante'.
Figure 2:
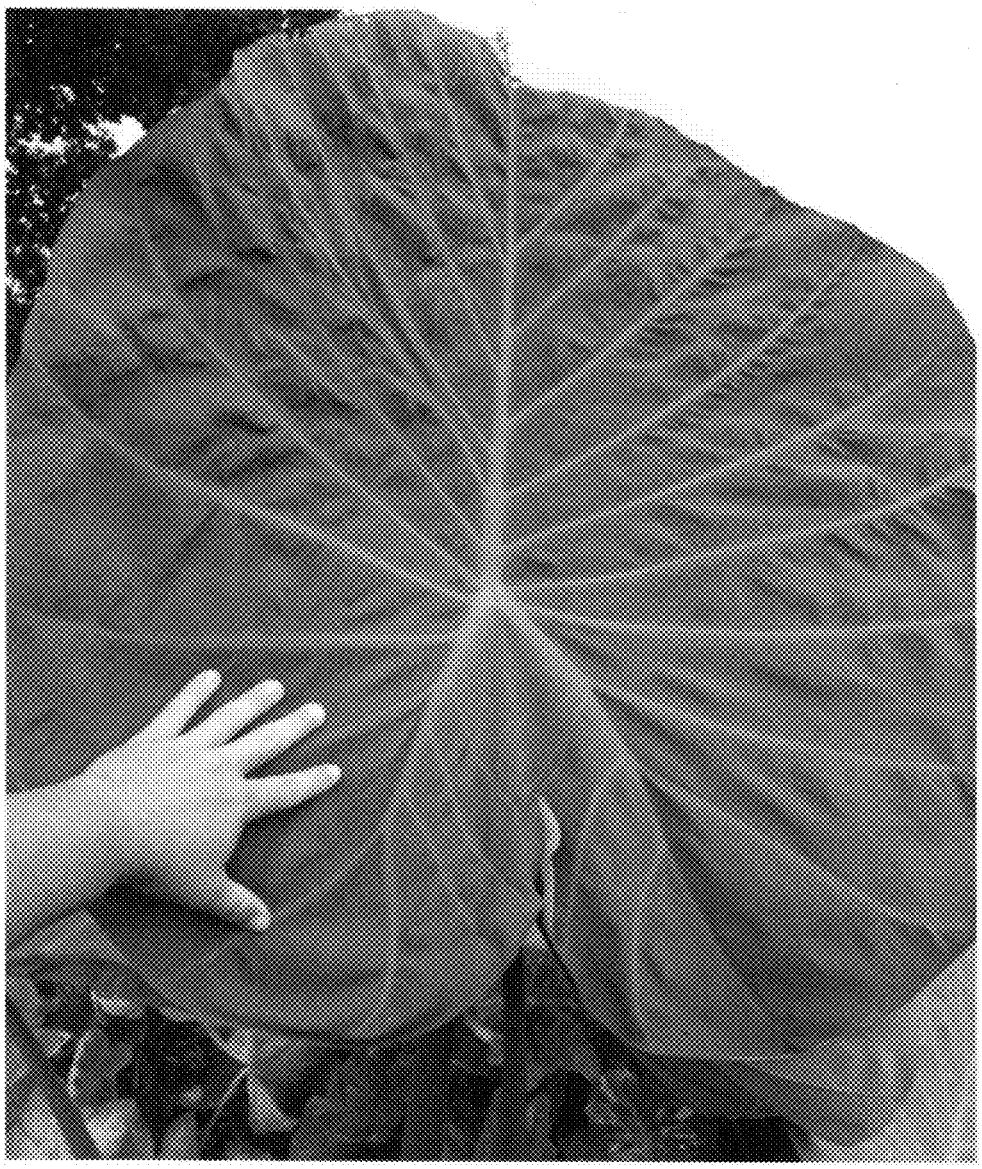

The photograph in FIG. 2 provides a view of the outside of the leaf of 'Fierce Gigante'.

The colors in the photographs are as close as possible with the photographic and printing technology utilized and the color values cited in the Detailed Botanical Description accurately describe the colors of the new *Colocasia*.

DETAILED BOTANICAL DESCRIPTION OF THE PLANT

The following is a detailed description of a plant 3-years in age of the new cultivar as grown outdoors in full sun under a 2-mm poly greenhouse in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—July to September in Louisville, Ky.

*Plant type*.—Tropical perennial.

*Plant habit*.—Upright, stemless.

*Height and spread*.—Reaches to 1.8 to 2.1 m (6 to 7 ft) in height and 0.9 to 1.5 to 2.1 m (5 to 7 ft) in width.

*Cold hardiness*.—At least to U.S.D.A. Zone 7a.

*Diseases and pests*.—No particular resistance or susceptibility has been observed.

*Rooting habit*.—Fleshy, medium in thickness, moderate density.

*Root initiation*.—Average of 2 to 6 weeks.

*Root description*.—Numerous fibrous hairs covering corm, shiny and dull texture and 165C overall in color, too numerous and wrapped around corm to measure the length, <0.5 mm in width.

*Tuberous rhizomes*.—Form at base of plant, 161C in color, up to 15 cm in length and 3 mm in diameter, dull texture.

*Propagation type*.—In vitro propagation using meristem tissue is preferred.

*Corm*.—Circular in shape, an average of 8 cm in diameter and height, overall 200B, fleshy part of corm a blend of 69A and N155C, bud of corm; detachable, circular to irregularly circular in shape, ranges is color between 63A and 65B and 200C, an average of 1 cm in diameter and height.

*Growth rate*.—Vigorous.

*Stem description*.—Stemless.

Foliage description:

*Leaf shape*.—Ovate-slightly oblong.

*Leaf division*.—Single.

*Leaf base*.—Cordate.

*Leaf apex*.—Acute, slightly cuspidate.

*Leaf venation*.—Pinnate, young upper and lower surface; 158A, mature upper (outer) surface, 142C with a round spot of 84A in the center of the leaf on the main intersecting veins, lower surface (inner); a blend of N77A and 60A and 71B.

*Leaf margins*.—Slightly undulate and cupped to form a bowl shape.

*Leaf attachment*.—Petiolate.

*Leaf arrangement*.—Alternate.

*Leaf surface*.—Upper and lower surface; glabrous and leathery.

*Leaf orientation*.—Held horizontally to upright on petiole.

*Leaf color*.—Young unexpanded inner and outer surface; blend of 145D and 154C, mature fully opened upper surface (outer); a blend of 131A and 143A and 142C, mature fully opened lower surface (inner); a blend of 140A and 140B and 141A.

*Leaf size*.—Young unexpanded leaf; 14 cm in length and 2 cm in diameter, young open leaf; up to 14 cm in length and 10 cm in width, depth of the sinus of the leaf blade is an average of 3 cm, mature leaf; an average of 92 cm in length and 76 cm in width.

*Petioles*.—Held erect to semi-erect, strong in strength; petiole (leaf) stalk; an average of 24 cm in length and 3 cm in diameter, glabrous and rubbery surface/texture, color; sheath edge; 1 cm in width, inside and outside surface is glabrous, color; matches petiole (leaf) stalk, petiole sheath; 24 cm in length, top section is 1 cm in diameter, mid section is 3 cm in diameter, bottom section is 4 cm in diameter, color of outer surface; base is a blend ranging between 181C to 181D and N77C and N77A with slight under tones of 73C, mid section to top is a blend ranging between 182A and N77C and N77A blending at the mid section and becoming a blend of 187A and N187A, color of inner surface; 65C, outer surface texture is glabrous and becomes dull when mature, inner surface texture is very glossy and fleshy.

Inflorescence description:

*Inflorescence type*.—Spadix surrounded by a spathe, male portion held above female portion, only female flowers were developed.

*Inflorescence size*.—Average of 31 cm in length and 8.5 cm in width.

*Inflorescence bud*.—Linear to slightly narrow oblanceolate in shape, an average of 31 cm in length and the male part is 2.5 cm in width, female part is 4 cm in width, male part is 187C at the base, becoming 160C at the midsection and to the top in color, female part is a blend of N187A and 187A with a overlay of N187B in color.

*Flower fragrance*.—A faint fruity, sweet and pleasant fragrance.

*Lastingness of inflorescence*.—Inflorescence blooms intermittently during the bloom period, individual flowers last about 2 to 3 weeks.

*Inflorescence/flower quantity*.—Intermittent throughout the bloom season, an average of 7, an average of 500 female flowers per spadix, male flowers were undeveloped.

*Spathe*.—Hooded, bract, subtending spadix, elliptic in shape, entire margin, acute apex, inner surface is coriaceous and smooth, outer surface is coriaceous and textured with linear grooves, 24 cm in length and 8.5 cm in width, lasts 5 to 7 days, color: outside when opening and fully open; part is 187C at the base, becoming 160C at the midsection and to the top in color, inner surface when opening and fully open; top 157A, blending into 160 at mid section and base.

*Spadix*.—Male portion above female zone, upright cylindrical shape (phallus-like), apex narrowly pointed with a slight bend, about 2 cm in diameter (not including ovary) and 16.5 cm in length, male zone; 1 cm in diameter and 12 in length, color immature and mature N92A, female zone; 2 cm in diameter and 5 cm in length, color immature and mature a blend of N92A and 84B.

*Peduncle*.—Emerges from base of plant, triangular in shape, up to 30.5 cm in length and 3 cm in diameter, held between an upright and 20° angle, durable and strong, a blend of N187A and 187A with an overlay of N187B in color, glabrous surface, strong in strength.

Reproductive organs:

*Gynoecium*.—Stigmas are a mix of N92 and 84B in color, ovary is flattened obovate in shape and 149A in color.

*Androcoecium*.—Undeveloped.

*Fruit and seed*.—Sterile.

It is claimed:

1. A new and distinct cultivar of *Colocasia* plant named 'Fierce Gigante' as herein illustrated and described.

* * * * *